(12) United States Patent
Faull et al.

(10) Patent No.: US 6,288,103 B1
(45) Date of Patent: Sep. 11, 2001

(54) INDOLE DERIVATIVES AS MCP-1 RECEPTOR ANTAGONISTS

(75) Inventors: Alan Wellington Faull; Andrew John Barker; Jason Grant Kettle, all of Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/485,107

(22) PCT Filed: Aug. 4, 1998

(86) PCT No.: PCT/GB98/02340

§ 371 Date: Feb. 3, 2000

§ 102(e) Date: Feb. 3, 2000

(87) PCT Pub. No.: WO99/07678

PCT Pub. Date: Feb. 18, 1999

(30) Foreign Application Priority Data

Aug. 7, 1997 (GB) .................................................. 9716656

(51) Int. Cl.[7] ...................... A61K 31/404; C07D 209/18
(52) U.S. Cl. ........................... 514/419; 548/465; 548/492
(58) Field of Search .................................. 548/465, 492; 514/419

(56) References Cited

U.S. PATENT DOCUMENTS

| | | | |
|---|---|---|---|
| 4,564,610 | * 1/1986 | Rahtz et al. | 514/80 |
| 4,840,963 | * 6/1989 | Shepard et al. | 514/418 |
| 5,254,563 | 10/1993 | Huth et al. | 514/292 |

FOREIGN PATENT DOCUMENTS

| | | |
|---|---|---|
| 39 43 225 | 6/1991 | (DE) . |
| WO 96/33171 | 10/1996 | (WO) . |

OTHER PUBLICATIONS

Conway et al., Heterocycles, 1992, 34(11), 2095–108.*
Sundberg et al., J. Org. Chem., 1973, 38(19), 3324–30.*
Yuusaku Yokoyama T al.: "Palladium–catalyzed cross–coupling reaction: direct allylation of aryl bromides with allyl acetate" Tetrahedron Letters., vol. 26, No. 52–1985 pp. 6457–6460, XP002081581 Oxford GB pp. 6458–6459: compound 7.
Chemical Abstracts, vol. 123, No. 14, Oct. 2, 1995 Columbus, Ohio, US; abstract No. 179521d, Kataoka, Kenichiro et al.: "Homopiperazines as cell migration inhibitors." Xp002081582 see abstract & JP 95 145060 A (Tejin Ltd). Chemical Abstracts, 118:147461, 1993.

* cited by examiner

Primary Examiner—Fiona T. Powers
(74) Attorney, Agent, or Firm—Pillsbury Winthrop LLP

(57) ABSTRACT

The invention concerns pharmaceutically useful indoles of formula (I), in which Z, X, T, A, $R^1$, $R^2$, p and q have any of the meanings defined herein, and their pharmaceutically acceptable salts or in vivo hydrolysable esters, as well as pharmaceutical compositions containing them. The novel compounds possess inhibitory activity against monocyte chemoattractant protein-1 (MCP-1). The invention further concerns the use of such indoles in the treatment of a disease or condition mediated by MCP-1.

(I)

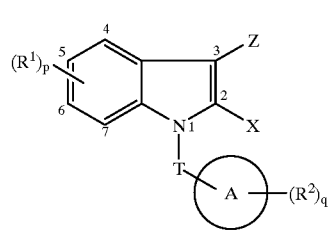

17 Claims, No Drawings

INDOLE DERIVATIVES AS MCP-1 RECEPTOR ANTAGONISTS

This application is the national phase of international application PCT/GB98/02340 filed Aug. 4, 1998 which desiganted the U.S.

The present invention relates to anti-inflammatory compounds that act via inhibition of Monocyte Chemoattractant Protein-1 (MCP-1) and in particular MCP-1 inhibitor compounds that contain an indole moiety. The invention further relates to processes for their preparation, to intermediates useful in their preparation, to their use as therapeutic agents and to pharmaceutical compositions containing them.

MCP-1 is a member of the chemokine family of pro-inflammatory cytokines which mediate leukocyte chemotaxis and activation. MCP-1 is a C—C chemokine which is one of the most potent and selective T-cell and monocyte chemoattractant and activating agents known. MCP-1 has been implicated in the pathophysiology of a large number of inflammatory diseases including rheumatoid arthritis, glomerular nephritides, lung fibrosis, restenosis (International Patent Application WO 94/09128), alveolitis (Jones et al., 1992, *J. Immunol.*, 149, 2147) and asthma. Other disease areas where MCP-1 is thought to play a part in their pathology are atherosclerosis (e.g. Koch et al., 1992, *J. Clin. Invest.*, 90, 772–779), psoriasis (Deleuran et al., 1996, *J. Dermatological Science*, 13,. 228–236), delayed-type hypersensitivity reactions of the skin, inflammatory bowel disease (Grinun et al., 1996, *J. Leukocyte Biol*, 59,. 804–812), multiple sclerosis and brain trauma (Berman et al, 1996, *J. Immunol.*, 156,. 3017–3023). An MCP-1 inhibitor may also be useful to treat stroke, reperfusion injury, ischemia, myocardial infarction and transplant rejection.

MCP-1 acts through the MCP-1 receptor (also known as the CCR2 receptor). MCP-2 and MCP-3 may also act, at least in part, through the MCP-1 receptor. Therefore in this specification, when reference is made to "inhibition or antagonism of MCP-1" or "MCP-1 mediated effects" this includes inhibition or antagonism of MCP-2 and/or MCP-3 mediated effects when MCP-2 and/or MCP-3 are acting through the MCP-1 receptor. Japanese patent application no. JP 04273857-A discloses indole compounds for treating hypertension with a phenyl sulphonyl moiety attached to the nitrogen of the indole ring. International patent application WO96/33171 discloses similar compounds for therapy of HIV-1 infections.

The present invention is based on the discovery of a class of compounds containing an indole moiety which have useful inhibitory activity against MCP-1.

Accordingly the present invention provides a compound of the formula (I)

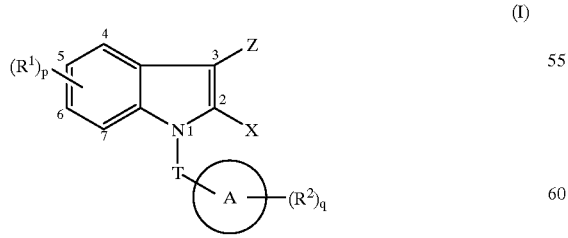

which is an inhibitor of monocyte chemoattractant protein-1 and wherein:

R$^1$ is independently selected from trifluoromethyl, C$_{1-4}$alkyl, halo, hydroxy, C$_{1-4}$alkoxy, C$_{1-4}$alkanoyloxy, amino, cyano, C$_{1-4}$alkylamino, di(C$_{1-4}$alkyl)amino, C$_{1-4}$alkanoylamino, nitro, carbamoyl, C$_{1-4}$alkoxycarbonyl, thiol, C$_{1-4}$alkylsulphanyl, C$_{1-4}$alkylsulphinyl, C$_{1-4}$alkylsulphonyl, sulphonamido, carbamoylC$_{1-4}$alkyl, N—(C$_{1-4}$alkyl)carbamoylC$_{1-4}$alkyl, N—(C$_{1-4}$alkyl)$_2$carbamoyl-C$_{1-4}$alkyl, hydroxyC$_{1-4}$alkyl, C$_{1-4}$alkoxyC$_{1-4}$alkyl, morpholino, pyrrolidinyl, carboxyC$_{1-4}$alkylamino, R$^3$ and —OR$^3$ (where R$^3$ is optionally substituted phenyl or an optionally substituted 5- or 6-membered heteroaryl ring);

p is 1–4 and R$^1$ can have the same or different values when p is 2–4;

T is of the formula

—(CHR$^4$)$_m$—(SO$_2$)—(CHR$^4$)$_s$—, (where R$^4$ is hydrogen or C$_{1-4}$alkyl, m=0–2, s=0–2, m+s=0–2, and R$^4$ can take different values when m+s=2);

X is carboxy, tetrazol-5-yl, cyano, SO$_3$H, —SO$_2$NHR$^4$ (where R$^4$ is as defined above), —SO$_2$NHAr (where Ar is an optionally substituted phenyl or optionally substituted 5 or 6 membered heteroaryl ring), —CONHR$^5$ (where R$^5$ is cyano, OH, —SO$_2$—C$_{1-4}$alkyl, —SO$_2$CF$_3$, —SO$_2$-phenyl, —(CHR$^4$)$_r$—COOH, (where r is 1–3 and R$^4$ (as defined above) can take different values when r is 2–3)), or X is a group of formula (II)

or X represents a group of formula (III)

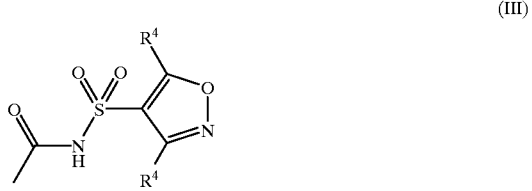

where the groups defined as R$^4$ here may have different values within the definition of R$^4$ above;

A is selected from phenyl, naphthyl, furyl, pyridyl and thienyl;

R$^2$ is independently selected from trifluoromethyl, C$_{1-4}$alkyl, halo, hydroxy, trifluoromethoxy, cyano, C$_{1-4}$alkoxy, C$_{1-4}$alkanoyl, C$_{1-4}$alkanoyloxy, amino, C$_{1-4}$alkylamino, di(C$_{1-4}$alkyl)amino, C$_{1-4}$alkanoylamino, nitro, carboxy, carbamoyl, C$_{1-4}$alkoxycarbonyl, thiol, C$_{1-4}$alkylsulphanyl, C$_{1-4}$alkylsulphinyl, C$_{1-4}$alkylsulphonyl, sulphonamido, carbamoylC$_{1-4}$alkyl, N—(C$_{1-4}$alkyl)carbamoylC$_{1-4}$alkyl, N—(C$_{1-4}$alkyl)$_2$carbamoyl-C$_{1-4}$alkyl, hydroxyC$_{1-4}$alkyl, C$_{14}$alkoxyC$_{1-4}$alkyl or two R$^2$ values together may form a divalent radical of the formula —O(CH$_2$)$_{1-4}$O— attached to adjacent carbon atoms on ring A;

q is 0–4 and R$^2$ can have the same or different values when q is 2–4;

Z is hydrogen, fluoro, chloro, bromo, iodo, methyl, trifluoromethyl, hydroxymethyl, methoxy, methylsulphanyl, methylsulphinyl, methylsulphonyl or carboxy$C_{3-6}$cycloalkyl, —(CHR$^4$)$_r$—NR$^6$R$^7$ (where r is 0–2, R$^6$ and R$^7$ are independently selected from H and C$_{1-4}$alkyl or R$^6$ and R$^7$ together with the nitrogen to which they are attached form a 5 or 6 membered non-aromatic ring optionally containing one further heteroatom selected from O, N or S); or a pharmaceutically acceptable salt or in vivo hydrolysable ester thereof.

In this specification the term 'alkyl' includes straight chained, branched structures and ring systems. For example, "C$_{1-4}$alkyl" includes propyl, isopropyl, t-butyl and cyclopropane. However, references to individual alkyl groups such as 'propyl' are specific for the straight chained version only, references to individual branched chain alkyl groups such as 'isopropyl' are specific for the branched chain version only and references to the cyclo groups such as cyclopropane are specific to the cyclic groups only. A similar convention applies to other radicals, for example "hydroxyC$_{1-4}$alkyl" includes 1-hydroxyethyl and 2-hydroxyethyl. The term "halo" refers to fluoro, chloro, bromo and iodo.

Suitable optional substituents for aryl and heteroaryl are any of the values defined for R$^1$ and R$^2$ above. "Aryl" means phenyl or naphthyl. "Heteroaryl" means an aromatic mono- or bicyclic-5–10 membered ring with up to three or five ring heteroatoms (in mono or bicyclic rings respectively) selected from nitrogen, oxygen and sulphur. Examples of "heteroaryl" include thienyl, pyrrolyl, furanyl, imidazolyl, thiazolyl, pyrimidinyl, pyridinyl, indolyl, benzimidazolyl, benzthiazolyl, quinolyl and isoquinolinyl.

An example of "C$_{1-4}$alkanoyloxy" is acetoxy. Examples of "C$_{1-4}$alkoxycarbonyl" include methoxycarbonyl, ethoxycarbonyl, n- and t-butoxycarbonyl. Examples of "C$_{1-4}$ alkoxy" include methoxy, ethoxy and propoxy. Examples of "C$_{1-4}$alkanoylamino" include formamido, acetamido and propionylamino. Examples of "C$_{1-4}$alkylsulphanyl" include methylthio and ethylthio. Examples of "C$_{1-4}$alkylsulphinyl" include methylsulphinyl and ethylsulphinyl. Examples of "C$_{1-4}$alkylsulphonyl" include methylsulphonyl and ethylsulphonyl. Examples of "C$_{1-4}$alkanoyl" include propanoyl and ethanoyl. Examples of "C$_{1-4}$alkylamino" include methylamino and ethylamino. Examples of "di(C$_{1-4}$alkyl)amino" include di-N-methylaamino, di-(N-ethyl)amino and N-ethyl-N-methylamino. Examples of "C$_{1-4}$alkoxyC$_{1-4}$ alkyl" methoxymethyl and propoxyethyl. Examples of "carbamoylC$_{1-4}$alkyl" are methylcarboxamide and ethylcarboxarnide. Examples of "carboxyC$_{3-6}$cycloalkyl" are 2-carboxycyclopropyl and 3-carboxycyclopentyl. Examples of "N—(C$_{1-4}$alkyl)carbamoylC$_{1-4}$alkyl" are methylaminocarbonylethyl and ethylaminocarbonylpropyl. Examples of "N—(C$_{1-4}$alkyl)$_2$carbamoyl-C$_{1-4}$alkyl" are dimethylaminocarbonylethyl and methylethylaminocarbonylpropyl. Examples of "carboxyC$_{1-4}$alkylamino" are carboxymethylamino and carboxypropylamino.

Preferred values for R$^1$, p, Z, X, T, A, R$^2$ and q are as follows.

Preferred values for R$^1$ are C$_{1-4}$alkoxy, halo, nitro, amino, trifluoromethyl and carboxyC$_{1-4}$alkylamino, more preferably chloro and/or C$_{1-4}$alkoxy. Where R$^1$ is halo, fluoro, chloro or bromo are preferred. Where R$^1$ is C$_{1-4}$alkoxy it is preferably methoxy or ethoxy, particularly methoxy. Preferably position 7 is unsubstituted, and preferably there is no more than one C$_{1-4}$alkoxy group.

Preferably p is 1 or 2.

Preferred combinations of p and R$^1$ are as follows.

When p=1 then R$^1$is preferably fluoro, chloro or methoxy and in particular 5-chloro and 6-chloro.

T is preferably —SO$_2$—.

Preferably X is carboxy, —CONHR$^5$ (where R$^5$ is —SO$_2$—C$_1$alkyl, —SO$_2$CF$_3$, —SO$_2$-phenyl) or tetrazol-5-yl. R$^5$ is preferably —SO$_2$CF$_3$. In particular X is carboxy.

Preferably A is phenyl, naphthyl, furyl and thienyl in particular phenyl or thienyl. When A is thienyl it is preferably thien-2-yl. Most preferably A is phenyl.

R$^2$ is preferably chloro, bromo, methyl, methoxy, nitro, trifluoromethyl or trifluoromethoxy. Another preferred value for R$^2$ is fluoro.

q is preferably 1 or 2, especially 2.

Preferred combinations of A, R$^2$ and q are as follows.

When A is phenyl, and q is 1, then R$^2$ is preferably chloro especially 3-chloro or 4-chloro. Other preferred values for R$^2$ include 3-fluoro, 4-fluoro and 3-trifluoromethyl.

When A is phenyl, and q is 2, then R$^2$ is preferably chloro, especially 3,4-dichlorophenyl. Another preferred value is fluoro, especially 3,4-difluoro.

When A is phenyl then the positions ortho to T are preferably unsubstituted.

When A is thien-2-yl then preferably R$^2$ is chloro, especially 5-chloro.

Preferably Z is hydrogen or bromo, especially hydrogen.

Therefore a preferred class of compounds is that of formula (I'):

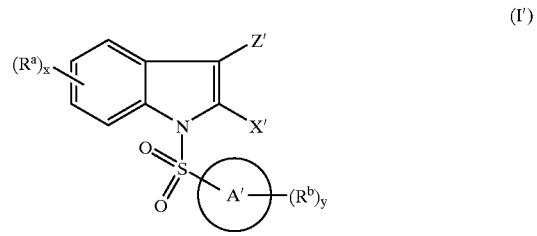

(I')

wherein;

R$^a$ is methoxy, fluoro, chloro, bromo, nitro, amino, trifluoromethyl or carboxymethylamino;

x is 1 or 2 with the proviso that there is at most one methoxy group;

X' is carboxy, —CONHSO$_2$CF$_3$ or tetrazol-5-yl;

A' is phenyl or thienyl;

R$^b$ is chloro, bromo, methyl, methoxy, nitro, trifluoromethyl or trifluoromethoxy;

y is 1 or 2;

Z' is hydrogen or bromo;

or a pharmaceutically acceptable salt or in vivo hydrolysable ester thereof.

Preferably R$^a$ is chloro or methoxy. Preferably position 7 is unsubstituted.

Preferred combinations of x and R$^a$ are as follows.

When x=1 then R$^a$ is preferably chloro or methoxy especially 5-chloro or 6-chloro.

Z' is preferably hydrogen.

A' is preferably phenyl. Where A' is thienyl it is preferably thien-2-yl.

Preferred combinations of A', R$^b$ and y are as follows.

When A' is phenyl, and y is 1, then R$^b$ is preferably chloro in particular 3-chloro or 4-chloro. Another preferred value is fluoro, in particular 3-fluoro or 4-fluoro.

When A' is phenyl, and y is 2, then R$^b$ is preferably chloro, in particular 3,4-dichlorophenyl. Another preferred value is fluoro, in particular 3,4-difluoro.

When A' is phenyl then the positions ortho to the SO$_2$ moiety linked to the indole ring are preferably hydrogen.

When A' is thien-2-yl then preferably $R^b$ is chloro in particular 5-chloro.

Preferred compounds having formula (I) or (IA) (defined below) include any one of:

N-(3,4-Dichlorophenylsulphonyl)-5-chloroindole-2-carboxylic acid;

N-(6-Bromonaphthalen-2-ylsulphonyl)-5-chloroindole-2-carboxylic acid;

N-(3-Chlorophenylsulphonyl)-5-chloroindole-2-carboxylic acid; and

3-Bromo-5-Fluoro-N-(3-trifluoromethylphenysulphonyl) indole-2-carboxylic acid;

or an in vivo hydrolysable ester or a pharmaceutically acceptable salt thereof.

Suitable pharmaceutically acceptable salts include acid addition salts such as methanesulfonate, fumarate, hydrochloride, hydrobromide, citrate, maleate and salts formed with phosphoric and sulphuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylarrine or amino acids for example lysine. There may be more than one cation or anion depending on the number of charged functions and the valency of the cations or anions. A preferred pharmaceutically acceptable salt is a sodium salt.

Some compounds of formula (I) may possess chiral centres. It is to be understood that the invention encompasses all such optical isomers and diastereoisomers of compounds of formula (I).

The invention further relates to all tautomeric forms of the compounds of formula (I).

It is also to be understood that certain compounds of the formula (I) car. exist in solvated as well as unsolvated forms such as, for example, hydrated forms. It is to be understood that the invention encompasses all such solvated forms.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Another aspect of the present invention provides a process for preparing a compound of formula (I) or a pharmaceutically acceptable salt or an in vivo hydrolysable ester thereof which process comprises of:

a) reacting compounds of formula (IV):

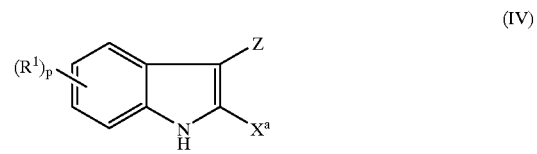

(IV)

where $X^a$ is carboxy protected in the form of an ester and other groups are as defined in formula (I) with a compound of formula (V):

(V)

where L is a leaving group other groups are as defined in formula (I) to give a compound of formula (VI):

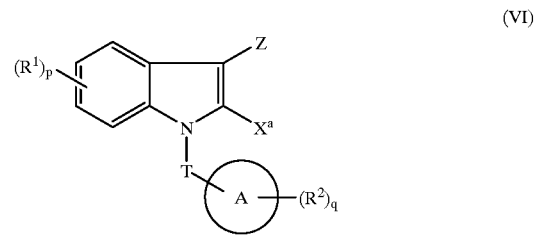

(VI)

where $X^a$ is carboxy protected as an ester; and b) optionally interconverting a compound of formula (VI) to give another compound of formula (VI), wherein any functional groups are protected if necessary and optionally:

i) removing any protecting groups;

ii) optionally forming a pharmaceutically acceptable salt or in vivo hydrolysable ester.

Compounds of formula (VI) and (I) may be interconverted for example as described herein or by known processes such as functional group modification or aromatic substitution.

L is a leaving group. Preferable values for L are chloro and bromo.

Compounds of formula (IV) and (V) may be reacted together in an inert solvent and a base such as N,N-dimethylformamide/sodium hydride or dichloromethane/sodium hydroxide (optionally in the presence of a phase transfer catalyst such as tetra-n-butylammonium hydrogensulphate) for 1–6 hours preferably 1–3 hours, at a temperature of 15–30° C., preferably 20–25° C. to give a compound of formula (VI).

Compounds of formula (IV) are commercially available, made by modification using known processes of commercially available compounds of formula (IV), or they are prepared by:

a) Reacting a compound of formula (VII):

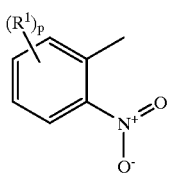
(VII)

where $R^1$ and p are as defined in formula (I), with a compound of formula (VIII)

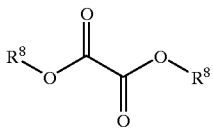
(VIII)

where $R^8$ is $C_{1-4}$alkyl.

Compounds of formula (VII) and (VIII) are reacted together under Reissert reaction conditions such as in an inert solvent (such as tetrahydrofuran), in the presence of a base (such as potassium ethoxide), at a temperature range of 15–30° C. preferably 20–25° C., for 10–20 hours preferably 15–17 hours. The resulting compound is isolated and dissolved in an alcohol such as ethanol and an organic acid (such as acetic acid) and a transition metal catalyst (such as 10% Pd/C) and cyclohexene is added. The mixture is heated at a temperature of 60–120° C. preferably at 70–90° C. for 15–25 hours preferably 16–20 hours to give a compound of formula (VI) in which Z is hydrogen. Then if desired Z can be optionally converted into another value of Z as defined in formula (I) using techniques known in the art such as those described below.

b) Reacting a compound of formula (IX):

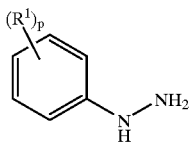
(IX)

where $R^1$ and p are as defined for formula (I), with a compound of formula (X):

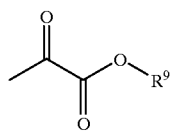
(X)

where $R^9$ is $C_{1-4}$alkyl.

Compounds of formula (IX) and (X) are reacted together under Fischer conditions such as with an organic acid (such as acetic acid), in an alcohol (such as ethanol), at a temperature of 60–90° C. preferably 75–85° C., for 1–5 hours preferably 1–3 hours. The compound is mixed with a strong acid (such as polyphosphoric acid) and heated at 90–150° C. preferably 100–120° C. for 0.54 hours preferably 0.5–2 hours to give a compound of formula (VI) in which Z is hydrogen. Then if desired Z can be optionally converted into another value of Z as defined in formula (I) using techniques known in the art such as those described below.

Compounds of formula (V), (VII), (VIII), (IX) and (X) are known or commercially available or are prepared by processes known in the art by standard manipulation of commercially available or known materials.

$R^8$ and $R^9$ are $C_{1-4}$alkyl. Preferably $R^8$ and $R^9$ are methyl or ethyl.

It will be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl. Specific examples of the substitution and modification reactions prior to or immediately following the processes mentioned above are illustrated, but not limited by, the following examples in which variable groups are as defined for formula (I) unless otherwise stated.

1) Modification of $R^1$.
a) For $R^1$=Ar: compounds of formula (XI)

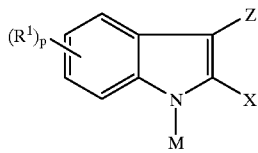
(XI)

M is H, a nitrogen protecting group or the group

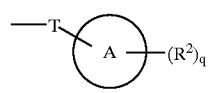

where $R^1$ is Br are coupled with compounds of formula (XI)

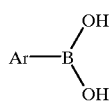
(XII)

where Ar is an optionally substituted phenyl or optionally substituted 5 or 6 membered heteroaryl ring, to give compounds of formula (XI) where $R^1$=Ar. Suitable reaction conditions are set out below.

Compounds of formula (XI) where $R^1$=Br and (XII) are reacted together in the presence of a transition metal catalyst (for example tetrakis(triphenylphosphine)palladium(0)), in an inert solvent (such as toluene) and an alcohol (such as ethanol), with an aqueous base (such as potassium carbonate), preferably in an inert atmosphere, at a temperature of 60–100° C. preferably 75–85° C. for 14–20 hours preferably 15–17 hours.

b) For $R^1$=$NH_2$; compounds of formula (XI) where $R^1$=$NO_2$ are reduced under standard conditions to give a compound of formula (XI) where $R^1$=$NH_2$. Suitable reaction conditions are set out below.

Compounds of formula (XI) where $R^1$=$NO_2$ are reacted with a reducing agent (such as sodium borohydride) and stannous chloride dihydrate in an alcohol (such as ethanol) at a temperature of 30–80° C. preferably 50–70° C. for 2–10 hours preferably 4–6 hours.

c) For $R^1$=MeC(O)NH—: compounds of formula (XI) where $R^1$=MeC(O)NH— can be prepared from compounds of formula (XI) where $R^1$=$NH_2$. Suitable reaction conditions are set out below.

Compounds of formula (XI) where $R^1$=$NH_2$ are reacted in acetic anhydride at a temperature of 60–140° C. preferably 80–100° C. for 0.5–5 hours preferably 0.5–2 hours.

d) For $R^1$=$C_{1-4}$alkoxycarbonyl$C_{1-4}$alkylamino: compounds of formula (XI) where $R^1$=$C_{1-4}$alkoxycarbonyl$C_{1-4}$alkylamino can be prepared from compounds of formula (XI) where $R^1$=$NH_2$. Suitable reaction conditions are set out below.

Compounds of formula (XI) where $R^1$=$NH_2$ are reacted with the corresponding glyoxalate, aldehyde ester or keto ester (such as ethyl glyoxalate) followed by the addition of a reducing agent (such as sodium cyanoborohydride) in an alcohol (such as ethanol) with an acid (such as acetic acid) for 1–10 minutes preferably 4–6 minutes at 15–30° C. preferably 20–25° C.

2) Modification of X.

a) For X=carboxy: hydrolysing a compound of formula (VI) as defined above to give a compound of formula (XIII):

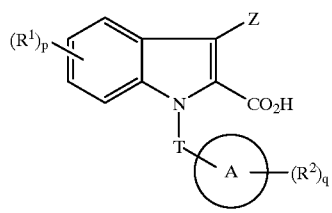

(XIII)

Suitable reaction conditions are set out below.

Compounds of formula (VI) where $X^a$ is —$CO_2Me$ may be conveniently hydrolysed to give compounds of formula (XIII) with a salt (such as lithium iodide), in an organic base (such as pyridine), at a temperature range of 100–125° C., in particular 115–120° C., for 3–10 hours, preferably 5–7 hours followed by the addition of aqueous acid (for example 2M hydrochloric acid).

b) For X=—$CONHR^5$ ($R^5$ is as defined for formula (I)): compounds where X=—$CONHR^5$ can be prepared by coupling compounds of formula (XIII) and compounds of formula (XIV):

 $R^5$—$NH_2$ (XIV)

under standard peptide coupling conditions. Suitable reaction conditions are set out below.

Compounds of formula (XIII) and compounds of formula (XIV) can be reacted together in the presence of a coupling agent (such as 1-ethyl-3-(3-dimethylaminopropyl) carbodiimide hydrochloride) and optionally a catalyst (such as dimethylamino pyridine) in an inert solvent (such as dichloromethane) for 1–36 hours preferably 20–30 hours at 15–30° C. preferably 20–25° C.

c) For X=C(O)$NH_2$ and CN: compounds of formula (XI) where X=C(O)$NH_2$ and CN can be prepared from compounds of formula (XI) where X=carboxy. Suitable reaction conditions are set out below.

Compounds of formula (XI) where X=carboxy are reacted with ammonia in an organic base (such as pyridine) with a sulphonating agent (such as methanesulphonyl chloride) at a temperature of −10 to 10° C. preferably −2 to 2° C. for 1–5 hours preferably 2–3 hours to give both compounds.

d) For X=tetrazol-5-yl: compounds of formula (XI) where X=tetrazol-5-yl can be prepared from compounds of formula (XI) where X=CN. Suitable reaction conditions are set out below.

Compounds of formula (XI) where X=CN are reacted with an azide (such as sodium azide) and triethylamine hydrochloride in a solvent (such as N-methyl pyrrolidinone) at a temperature of 100–200° C. preferably 140–160° C. for 3–10 hours preferably 5–6 hours.

3) Modification of Z.

a) For Z=Br: compounds of formula (XI) where Z=hydrogen may be brominated under standard conditions to give a compound of formula (XI) where Z=Br. Suitable reaction conditions are set out below.

Compounds of formula (XI) where Z=bromine may be prepared by reacting a compound of formula (XI) where Z=hydrogen in an inert solvent (such as N,N-dimethylformnamide) with bromine for 5–55 minutes particularly 25–35 minutes at 10–30° C., preferably 20–25° C.

Other modifications of Z are achieved by standard reactions known in the art. For example:

a) a substituent of the formula —$CH_2NR_2$ can be prepared by the Mannich reaction.

Compounds of formula (XI) where Z=hydrogen are treated with formaldehyde and an amine in the presence of acid;

b) the Vilsmeier formulation of compounds of formula (XI) where Z=hydrogen with $POCl_3$ and N,N-dimethylformamide gives the aldehyde in the three position which can then be selectively reduced to the carbinol (with $NaBH_4$) or to the methyl (with $NaBH_4$ and trifluoroacetic acid) under standard reaction conditions.

The reader is also directed to Japanese patent application no. JP 04273857-A and International patent application WO 96/33171 for synthetic details of sulphonyl indole compounds.

It will also be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

When a pharmaceutically-acceptable salt of a compound of the formula (I) is required, it may be obtained, for example, by reaction of said compound with the appropriate acid (which affords a physiologically acceptable anion), or with the appropriate base (which affords a physiologically acceptable cation), or by any other conventional salt formation procedure.

When an optically active form of a compound of the formula (I) is required, it may be obtained, for example, by carrying out one of the aforesaid procedures using an optically active starting material or by resolution of a racemic form of said compound using a conventional procedure.

According to a further aspect of the invention there is provided a compound of the formula (I) as defined herein, or a pharmaceutically acceptable salt or an in vivo hydrolysable ester thereof, for use in a method of treatment of the human or animal body by therapy.

The invention also provides a compound of formula (I) as defined herein, or a pharmaceutically acceptable salt, or an in vivo hydrolysable ester thereof, for use as a medicament.

Another aspect of the present invention provides the use of a compound of formula (1) or a pharmaceutically acceptable salt or an in vivo hydrolysable ester thereof, in the manufacture of a medicament for use in antagonising an MCP-1 mediated effect in a warm blooded animal, such as man.

Another aspect of the present invention provides the use of a compound of formula

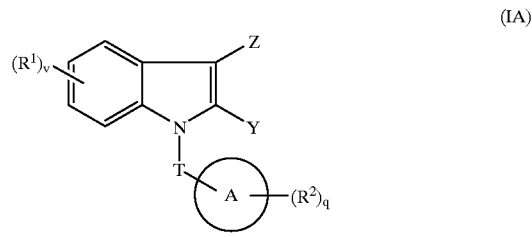

(IA)

where
R$^1$, Z, T, A, R$^2$ and q are as defined for formula (I);
Y=X (as defined for formula (I)) or —CONHR$^{10}$(where R$^{10}$ is H or C$_{1-4}$alkyl);
v=0–4;

a pharmaceutically acceptable salt or an in vivo hydrolysable ester thereof, in the manufacture of a medicament for use in antagonising an MCP-1 mediated effect in a warm blooded animal, such as man.

A further aspect of the present invention comprises a novel compound of the formula (IA) or a pharmaceutically acceptable salt thereof or an in vivo hydrolysable ester thereof, for example a compound of the formula (IA) as defined above in which Y is carboxy, T is —SO$_2$—, A(R$^2$)$_q$ is phenyl independently substituted at the 3 and 4 positions by halogeno (such as 3,4-dichlorophenyl or 3,4-difluorophenyl), v is 1 or 2 and R$^1$ is attached at the 4 and/or 5 position of the indole ring. Particular novel compounds of formula (IA) include, for example, N-(3-chlorophenylsulphonyl)indole-2-carboxylic acid;
N-(3,4-Dichlorophenylsulphonyl)indole-2-carboxylic acid;
N-(4,5-Dichlorothien-2-ylsulphonyl)indole-2-carboxylic acid;
3-Bromo-N-(3-trifluoromethylphenylsulphonyl)indole-2-carboxylic acid; and
3-Chloro-N-(3-trifluoromethylphenylsulphonyl)indole-2-carboxylic acid;

or a pharmaceutically acceptable salt thereof or an in vivo hydrolysable ester thereof.

According to a further aspect of the present invention there is provided a method for antagonising an MCP-1 mediated effect in a warm blooded animal, such as man, in need of such treatment, which comprises administering to said animal an effective amount of a compound of formula (IA), or a pharmaceutically acceptable salt, or an in vivo hydrolysable ester thereof. According to a further aspect of the invention there is provided a method of inhibiting the binding of MCP-1 to a receptor thereof in a warm blooded animal in need thereof which comprises administering to said animal an effective amount of a compound of formula (I) or (IA), or a pharmaceutically acceptable salt, or an in vivo hydrolysable ester thereof. According to a further aspect of the invention there is provided the use of a compound of formula (I) or (IA) for the manufacture of a medicament for use in inhibiting the binding of MCP-1 to a receptor thereof.

In order to use a compound of the formula (I) (or (IA)) or a pharmaceutically acceptable salt or an in vivo hydrolysable ester thereof for the therapeutic treatment of mammals including humans, in particular in treating inflammation, it is normally formulated in accordance with standard pharmaceutical practice as a pharmaceutical composition.

Therefore in another aspect the present invention provides a pharmaceutical composition which comprises a compound of the formula (I) (or novel compound of formula (IA)) or a pharmaceutically acceptable salt or an in vivo hydrolysable ester thereof and a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more coloring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil. Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in, the art.

Compositions for administration by insufflation may be in the form of a finely divided powder containing particles of average diameter of, for example, $30\mu$ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of rats.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The following illustrate, but are not intended to limit, representative pharmaceutical dosage forms of the invention as defined herein (the active ingredient being termed "Compound X"), for therapeutic or prophylactic use in humans:

(a)

| Tablet I | mg/tablet |
|---|---|
| Compound X. | 100 |
| Lactose Ph.Eur | 182.75 |
| Croscarmellose sodium | 12.0 |
| Maize starch paste (5% w/v paste) | 2.25 |
| Magnesium stearate | 3.0 |

(b)

| Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

(c)

| Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

(d)

| Capsule | mg/capsule |
|---|---|
| Compound X | 10 |
| Lactose Ph.Eur | 488.5 |
| Magnesium | 1.5 |

(e)

| Injection I | (50 mg/ml) |
|---|---|
| Compound X | 5.0% w/v |
| 1M Sodium hydroxide solution | 15.0% v/v |
| 0.1M Hydrochloric acid | to adjust pH to 7.6 |
| Polyethylene glycol 400 | 4.5% w/v |
| Water for injection | to 100% |

(f)

| Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection | to 100% |

(g)

| Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

(h)

| Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

(i)

| Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

(j)

| Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

-continued (k)

| Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

(l)

| Ointment | ml |
|---|---|
| Compound X | 40 mg |
| Ethanol | 300 µl |
| Water | 300 µl |
| 1-Dodecylazacycloheptan-2-one | 50 µl |
| Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

Biological Testing.

Abbreviations:

| ATCC | American Type Culture Collection, Rockville, USA. |
|---|---|
| BCA | bicinchroninic acid, (used, with copper sulphate, to assay protein) |
| DMEM | Dulbecco's modified Eagle's medium |
| EGTA | ethylenebis(oxyethylenenitrilo)tetraacetic acid |
| FCS | foetal calf serum |
| HBSS | Hank's Balanced Salt Solution |
| hMCP-1 | human Monocyte Chemoattractant Protein-1 |
| PBS | phosphate buffered saline |
| PCR | polymerase chain reaction |

AMPLITAQ™, available from Perkin-Elmer Cetus, is used as the source of thermostable DNA polymerase.

Binding Buffer is 50 mM HEPES, 1 mM $CaCl_2$, 5 mM $MgCl_2$, 0.5% foetal calf serum, adjusted to pH 7.2 with 1 M NaOH.

Non-Essential Amino Acids (100× concentrate) is: L-Alanine, 890 mg/l; L-Asparagine, 1320 mg/l; L-Aspartic acid, 1330 mg/l; L-Glutamic acid, 1470 mg/l; Glycine, 750 mg/l; L-Proline, 1150 mg/l and; L-Serine, 1050 mg/l.

Hypoxanthine and Thymidine Supplement (50× concentrate) is: hypoxanthine, 680 mg/l and; thymidine, 194 mg/l.

Penicillin-Streptomycin is: Penicillin G (sodium salt); 5000 units/ml; Streptomycin sulphate, 5000 µg/ml.

Human monocytic cell line THP-1 cells are available from ATCC, accession number ATCC TIB-202.

Hank's Balanced Salt Solution (HBSS) was obtained from Gibco; see *Proc. Soc. Exp. Biol. Med.,* 1949, 71, 196.

Synthetic cell culture medium, RPMI 1640 was obtained from Gibco; it contains inorganic salts [$Ca(NO_3)_2.4H_2O$ 100 mg/l; KCl 400 mg/l; $MgSO_4.7H_2O$ 100 mg/l; NaCl 6000 mg/l; $NaHCO_3$ 2000 mg/l & $Na_2HPO_4$ (anhyd) 800 mg/l], D-Glucose 2000 mg/l, reduced glutathione 1 mg/l, amino acids and vitamins.

FURA-2/AM is 1-[2-(5-carboxyoxazol-2-yl)-6-aminobenzofuran-5-oxy]-2-(2'-amino-5'-methylphenoxy)-ethane-N,N,N',N'-tetraacetic acid pentaacetoxymethyl ester and was obtained from Molecular Probes, Eugene, Oreg., USA.

General molecular biology procedures can be followed from any of the methods described in "Molecular Cloning-A Laboratory Manual" Second Edition, Sambrook, Fritsch and Maniatis (Cold Spring Harbor Laboratory, 1989).

Biological Assays for hMCP-1 Antagonists a) hMCP-1 Receptor-binding Assay i) Cloning and Expression of hMCP-1 Receptor The MCP-1 receptor B (CCR2B) cDNA was cloned by PCR from THP-1 cell RNA using suitable oligonucleotide primers based on the published MCP-1 receptor sequences (Charo et al., 1994, *Proc. Natl. Acad. Sci. USA,* 91, 2752). The resulting PCR products were cloned into vector PCR-II™ (InVitrogen, San Diego, Calif.). Error free CCR2B cDNA was subcloned as a Hind III-Not I fragment into the eukaryotic expression vector pCDNA3 (In Vitrogen) to generate pCDNA3/CC-CKR2A and pCDNA3/CCR2B respectively.

Linearised pCDNA3/CCR2B DNA was transfected into CHO-K1 cells by calcium phosphate precipitation (Wigler et al., 1979, *Cell,* 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, *Prot. Express. Purific.,* 6, 134). CHO-K1 clone 7 (CHO-CCR2B) was identified as the highest MCP-1 receptor B expressor.

ii) Preparation of Membrane Fragments

CHO-CCR2B cells were grown in DMEM supplemented with 10% foetal calf serum, 2 mM glutamine, 1× Non-Essential Amino Acids, 1× Hypoxanthine and Thymidine Supplement and Penicillin-Streptomycin (at 50 µg streptomycin/mi, Gibco BRL). Membrane fragments were prepared using cell lysis/differential centrifugation methods as described previously (Siciliano et al., 1990, *J. Biol. Chem.,* 265, 19658). Protein concentration was estimated by BCA protein assay (Pierce, Rockford, Ill.) according to the manufacturer's instructions.

iii) Assay $^{125}$I MCP-1 was prepared using Bolton and Hunter conjugation (Bolton et al., 1973, *Biochem. J.,* 133, 529; Amersham International plc]. Equilibrium binding assays were carried out using the method of Ernst et al., 1994, *J. Immunol.,* 152, 3541. Briefly, varying amounts of $^{125}$I-labeled MCP-1 were added to 10 mg of purified CHO-CCR2B cell membranes in 100 ml of Binding Buffer. After 1 hour incubation at room temperature the binding reaction mixtures were filtered and washed 5 times through a plate washer (Packard Harvester Filtermate™ 196). Scintillation fluid (25 µl, Microscint™-20, a high efficiency liquid scintillation counting cocktail for aqueous samples) was added to each well and the plate was covered with plate sealer and counted (Packard Top Count™). Cold competition studies were performed as above using 100 pM $^{125}$I-labeled MCP-1 in the presence of varying concentrations of unlabelled MCP-1. Non-specific binding was determined by the inclusion of a 200-fold molar excess of unlabelled MCP-1 in the reaction.

Ligand binding studies with membrane fragments prepared from CHO-CCR2B cells showed that the CCR2B was present at a concentration of 0.2 pmoles/mg of membrane protein and bound MCP-1 selectively and with high affinity ($IC_{50}$=110 pM, $K_d$=120 pM). Binding to these membranes was completely reversible and reached equilibrium after 45 minutes at room temperature, and there was a linear relationship between MCP-1 binding and CHO-CCR2B cell membrane concentration when using MCP-1 at concentrations between 100 pM and 500 pM.

Test compounds dissolved in DMSO (5 µl) were tested in competition with 100 pM labelled MCP-1 over a concentration range (0.1–200 µM) in duplicate using eight point dose-response curves and $IC_{50}$ concentrations were calculated.

b) MCP-1 Mediated Calcium Flux in THP-1 Cells

The human monocytic cell line THP-1 was grown in a synthetic cell culture medium RPMI 1640 supplemented with 10% foetal calf serum, 2 mM glutamine and Penicillin-Streptomycin (at 50 µg streptomycin/ml, Gibco BRL). THP-1 cells were washed in HBSS (lacking $Ca^{2+}$ and $Mg^{2+}$)+1 mg/ml BSA and resuspended in the same buffer at a density of $3 \times 10^6$ cells/ml. The cells were then loaded with 1 mM FURA-2/AM for 30 min at 37° C., washed twice in HBSS, and resuspended at $1 \times 10^6$ cells/ml. THP-1 cell suspension (0.9 ml) was added to a 5 ml disposable cuvette containing a magnetic stirrer bar and 2.1 ml of prewarmed (37° C.) HBSS containing 1 mg/ml BSA, 1 mM $MgCl_2$ and 2 mM $CaCl_2$. The cuvette was placed in a fluorescence spectrophotometer (Perkin Elmer, Norwalk, Conn.) and preincubated for 4 min at 37° C. with stirring. Fluorescence was recorded over 70 sec and cells were stimulated by addition of hMCP-1 to the cuvette after 10 sec. $[Ca^{2+}]i$ was measured by excitation at 340 nm and 380 nm alternately and subsequent measurement of the intensity of the fluorescence emission at 510 nm. The ratio of the intensities of the emitted fluorescent light following excitation at 340 nm and 380 nm, (R), was calculated and displayed to give and estimate of cytoplasmic $[Ca^{2+}]$ according to the equation:

$$[Ca^{2+}]i = K_d \frac{(R - R\min)}{(R\max - R)}(Sf2/Sb2)$$

where the $K_d$ for FURA-2 $Ca^{2+}$ complex at 37° C. was taken to be 224 nm. $R_{max}$ is the maximal fluorescence ratio determined after addition of 10 mM Ionomycin, $R_{min}$ is the minimal ratio determined by the subsequent addition of a $Ca^{2+}$ free solution containing 5 mM EGTA, and Sf2/Sb2 is the ratio of fluorescence values at 380 nm excitation determined at $R_{min}$ and $R_{max}$, respectively.

Stimulation of THP-1 cells with hMCP-1 induced a rapid, transient rise in $[Ca^{2+}]i$ in a specific and dose dependent manner. Dose response curves indicated an approximate $EC_{50}$ of 2 nm. Test compounds dissolved in DMSO (10 µl) were assayed for inhibition of calcium release by adding them to the cell suspension 10 sec prior to ligand addition and measuring the reduction in the transient rise in $[Ca^{2+}]i$. Test compounds were also checked for lack of agonism by addition in place of hMCP-1.

c) hMCP-1 Mediated Chemotaxis Assay

In vitro chemotaxis assays were performed using either the human monocytic cell line THP-1 or peripheral blood mixed monocytes obtained from fresh human blood purified by erythrocyte sedimentation followed by density gradient centrifugation over 9.6% (w/v) sodium metrizoate and 5.6% (w/v) polysaccharide, density 1.077 g/mn (Lymphopre™ Nycomed). Cell migration through polycarbonate membranes was measured by enumerating those passing through either directly by Coulter counting or indirectly by use of a colourimetric viability assay measuring the cleavage of a tetrazolium salt by the mitochondrial respiratory chain (Scudiero D. A. et al. 1988, *Cancer Res.*, 48, 4827–4833).

Chemoattractants were introduced into a 96-well microtiter plate which forms the lower well of a chemotaxis chamber fitted with a PVP-free 5 µm poresize polycarbonate adhesive framed filter membrane (NeuroProbe MB series, Cabin John, Md. 20818, USA) according to the manufacturer's instructions. The chemoattractant was diluted as appropriate in synthetic cell culture medium, RPMI 1640 (Gibco) supplemented with 2 mM glutamine and 0.5% BSA. Each dilution was degassed under vacuum for 30 min and was placed (400 µl) in the lower wells of the chamber and THP-1 cells ($5 \times 10^5$ in 100 µl RPMI 1640+0.5% BSA) were incubated in each well of the upper chamber. For the inhibition of chemotaxis the chemoattractant was kept at a constant submaximal concentration determined previously for each chemokine and added to the lower well together with the test compounds dissolved in DMSO (final DMSO concentration<0.05% v/v) at varying concentrations. The chamber was incubated for 2 h at 37° C. under 5% $CO_2$. The medium was removed from the upper wells which were then washed out with 200 µl physiological saline before opening the chamber, wiping dry the membrane surface and centrifuging the 96-well plate at 600 g for 5 min to harvest the cells. Supernatant (150 µl) was aspirated and 10 µl of cell proliferation reagent, WST-1, {4-[3-(4-iodophenyl)-2-(4-nitrophenyl)-2H-5-tetrazolio]-1,3-phenyl disulfonate} plus an electron coupling reagent (Boehringer Mannheim, Cat.no. 1644 807) was added back to the wells. The plate was incubated at 37° C. for 3 h and the absorbance of the soluble formazan product was read on a microtitre plate reader at 450 nm. The data was input into a spreadsheet, corrected for any random migration in the absence of chemoattractant and the average absorbance values, standard error of the mean, and significance tests were calculated. hMCP-1 induced concentration dependent cell migration with a characteristic biphasic response, maximal 0.5–1.0 nm.

Compounds tested of the present invention generally had $IC_{50}$ values of less than 50 µM in the hMCP-1 receptor binding assay described herein. For example the compound of example 2.01 had an $IC_{50}$ of 10 µM.

The invention is further illustrated, but not limited by the following Examples.

General Procedures

N,N-Dimethylformamide (DMF) was dried over 4 Å molecular sieves. Anhydrous tetrahydrofuran (THF) was obtained from Aldrich SURESEAL™ bottles. Other commercially available reagents and solvents were used without further purification unless otherwise stated. Organic solvent extracts were dried over anhydrous $MgSO_4$. $^1H$, $^{13}C$ and $^{19}F$ NMR were recorded on Bruker WM200, WM250, WM300 or WM400 instruments using $Me_2SO$-$\delta_6$ with $Me_4Si$ or $CCl_3F$ as internal standard as appropriate, unless otherwise stated. Chemical shifts are in δ (ppm) and peak multiplicities are designated as follows: s, singlet; d, doublet; dd, doublet of doublets; t, triplet; dt, doublet of triplets; q, quartet; m, multiplet; br, broad. Mass spectra were recorded on VG 12—12 quadrupole, VG 70–250 SE, VG ZAB 2-SE or a VG modified AEI/Kratos MS9 spectrometers. For TLC analysis, Merck precoated TLC plates (silica gel 60 F254, d=0.25 mm) were used. Flash chromatography was performed on silica (Merck Kieselgel: Art.9385). Melting point determinations were performed on a Kofler block or with a Büchi melting point apparatus and are uncorrected. All temperatures are in degrees centigrade.

EXAMPLE 1

Methyl N-(3,4-dichlorophenylsulphonyl)indole-2-carboxylate

Methyl indole-2-carboxylate (0.15 g) was dissolved in DMF and sodium hydride (41 mg) was added in a single portion. The reaction was stirred for 1 hour, then 3,4-dichlorobenzenesulphonyl chloride (0.25 g) was added in a single portion. Stirring was continued for a further 2 hours and then the reaction was quenched by the addition of water. The reaction mixture was partitioned between water and ethyl acetate. Combined organic extracts were dried (MgSO$_4$) and concentrated in vacuo and the residue purified by column chromatography using isohexane-5% ethyl acetate as eluent to give the desired end product as a solid (51%). NMR δ (CDCl$_3$) 3.96 (s, 3H), 7.22–8.20 (m, 8H); M/z (+) 384 (MH$^+$), 352, 175.

EXAMPLES 1.01–1.05

The procedure described in Example 1 was repeated using the appropriate indole-2-carboxylic ester and arylsulphonyl halide. Thus there were obtained the compounds described below.

EXAMPLE 1.01

Methyl N-(3-chlorophenylsulphonyl)indole-2-carboxylate in 82% yield

NMR δ (CDCl$_3$) 3.91 (s, 3H), 7.20–8.14 (m, 9H); M/z (+) 350 (MH$^+$), 318, 175, 144.

EXAMPLE 1.02

Methyl N-(4,5-dichlorothien-2-ylsulphonyl)indole-2-carboxylate in 19% yield

NMR δ (CDCl$_3$) 3.98 (s, 3H), 7.22–8.08 (m, 6H); M/z (+) 390 (MH$^+$), 358, 175, 144.

EXAMPLE 1.03

Methyl 5-chloro-N-(3,4-dichlorophenylsulphonyl)indole-2-carboxylate in 24% yield NMR δ (CDCl$_3$) 3.87 (s, 3H), 7.44 (s, 1H), 7.54 (dd, 1H), 7.82 (d, 1H), 7.96 (m, 2H), 8.12 (d, 1H), 8.28 (d, 1H).

EXAMPLE 1.04

Methyl N-(6-bromonapthalen-2-ylsulphonyl)-5-chloroindole-2-carboxylate in 9% yield NMR δ (CDCl$_3$) 3.88 (s, 3H), 7.39 (s, 1H), 7.52 (dd, 1H), 7.78 (d, 1H), 7.84 (dd, 1H), 7.94 (dd, 1H), 8.12 (m, 2H), 8.20 (d, 1H), 8.35 (s, 1H), 8.82 (s, 1H).

EXAMPLE 1.05

Methyl N-(3-chlorophenylsulphonyl)-5-chloroindole-2-carboxylate in 24% yield

NMR δ (CDCl$_3$) 3.87 (s, 3H), 7.41 (s, 1H), 7.53 (dd, 1H), 7.68 (t, 1H), 7.82 (m,2H), 7.98 (d, 1H), 8.04 (s, 1H), 8.09 (d, 1H).

EXAMPLE 1.06

Methyl 3-bromo-N-(3-trifluoromethylphenylsulphonyl)indole-2-carboxylate in 31% yield NMR δ (CD$_3$SOCD$_3$) 3.96 (s, 3H), 7.46 (t, 1H), 7.57 (dd, 1H), 7.62 (d, 1H), 7.88 (t, 1H), 8.1 (d, 1H), 8.14 (d, 1H), 8.21 (s, 1H), 8.26 (d, 1H).

EXAMPLE 1.07

Methyl 4-acetoxy-N-(3,4-dichlorophenylsulphonyl)indole-2-carboxylate in 65% yield NMR δ (CD$_3$SOCD$_3$) 2.34 (s, 3H), 3.86 (s, 3H), 7.16 (d, 1H), 7.50 (s, 1H), 7.55 (t, 1H), 7.92–8.06 (m, 3H), 8.31 (d, 1H); M/z (+) 442 (MH$^+$).

EXAMPLE 1.08

Methyl 3-chloro-N-(3-trifluoromethylphenylsulphonyl)indole-2-carboxylate in 68% yield NMR δ (CD$_3$SOCD$_3$) 3.96 (s, 3H), 7.48 (t, 1H), 7.59–7.68 (m, 2H), 7.88 (t, 1H), 8.1–8.16 (m, 2H), 8.2 (s, 1H), 8.26 (d, 1H); M/z (+) 418 (MH$^+$).

EXAMPLE 1.09

Methyl 3-chloro-5-fluoro-N-(3-trifluoromethylphenylsulphonyl)indole-2-carboxylate in 34% yield NMR δ (CD$_3$SOCD$_3$) 3.98 (s, 3H), 7.37–7.49 (m, 2H), 7.89 (t, 1H), 8.13–8.18 (m, 2H), 8.22 (s, 1H), 8.27 (d, 1H).

EXAMPLE 2

N-(3-chlorophenylsulphonyl)indole-2-carboxylic acid

Methyl N-(3-chlorophenylsulphonyl)indole-2-carboxylate (0.56 g) and lithium iodide (2.0 g) were dissolved in pyridine and heated at reflux for 6 hours, cooled to room temperature and poured into 2M HCl and extracted with diethyl ether. Combined organic extracts were dried (MgSO$_4$) and concentrated in vacuo to give an oil which was purified by column chromatography using DCM-2% methanol as eluent to give the desired product as a white solid (0.24 g, 45%), mp 216–217°; NMR δ (CD$_3$SOCD$_3$) 7.30–8.10 (m, 9H); M/z(−) 334 (M−H$^+$), 290, 226, 191, 180, 116.

EXAMPLES 2.01–2.05

The procedure described in Example 2 was repeated using the appropriate indole-2-carboxylic ester. Thus there were obtained the compounds described below.

EXAMPLE 2.01

N-(3,4-Dichlorophenylsulphonyl)indole-2-carboxylic acid in 74% yield mp 203–204°; NMR δ (CD$_3$SOCD$_3$) 7.30 (m, 2H), 7.5 (m, 1H), 7.7 (m, 1H), 7.9 (m, 1H), 8.0 (m, 2H), 8.25 (m, 1H); M/z(−) 370 (M$^+$),

EXAMPLE 2.02

N-(4.5-Dichlorothien-2-ylsulphonyl)indole-2-carboxylic acid in 75% yield mp 82–183°; NMR δ (CD$_3$SOCD$_3$) 8.25 (s, 1H), 7.95 (d, 1H), 7.63 (d, 1H), 7.42 (t, 1H), 7.25 (t, 1H), 7.10 (m, 1H); M/z(−) 376 (M$^+$), 374,332, 330, 268, 266, 233, 231.

EXAMPLE 2.03

N-(3,4-Dichlorophenylsulphonyl)-5-chloroindole-2-carboxylic acid in 57% yield

NMRδ (CD$_3$SOCD$_3$) 7.12 (s, 1H), 7.44 (dd, 1H), 7.72 (d, 1H), 7.88 (d, 1H), 8.02 (d, 1H), 8.08 (dd, 1H), 8.38 (s, 1H); M/z(−) 404 (M−H$^+$), 358.

EXAMPLE 2.04

N-(6-Bromonaphthalen-2-ylsulphonyl)-5-chloroindole-2-carboxylic acid in 68% yield NMR δ (CD$_3$SOCD$_3$) 6.92 (s,1H), 7.36 (dd, 1H), 7.64 (s, 1H), 7.80 (dd, 1H), 8.07 (m, 2H), 8.16 (m, 2H), 8.32 (s, 1H), 8.86 (s, 1H); M/z(−) 466 (M−H$^+$), 464, 462, 418.

EXAMPLE 2.05

N-(3-Chlorophenylsulphonyl)-5-chloroindole-2-carboxylic acid in 68% yield

NMR δ (CD$_3$SOCD$_3$) 7.26 (s, 1H), 7.48 (dd, 1H), 7.66 (t, 1H), 7.77 (s, 1H), 7.82 (d, 1H), 8.05 (t, 2H), 8.12 (s, 1H); M/z(−) 368 (M−H$^+$), 324.

EXAMPLE 2.06

3-Bromo-N-(3-trifluoromethylphenylsulphonyl)indole-2-carboxylic acid in 50% yield NMR δ (CD$_3$SOCD$_3$) 7.42 (t, 1H), 7.5–7.59 (m, 2H), 7.88 (t, 1H), 8.08 (d, 1H), 8.12 (d, 1H), 8.32–8.38 (m, 2H); M/z(−) 446 (M−H$^+$), 402, 322.

EXAMPLE 2.07

3-Chloro-N-(3-trifluoromethylphenylsulphonyl)indole-2-carboxylic acid in 58% yield NMR δ (CD$_3$SOCD$_3$) 7.45 (s, 1H), 7.56 (d, 1H), 7.62 (d, 1H), 7.88 (t, 1H), 8.11 (t, 2H), 8.28–8.36 (m, 2H); M/z(−) 402 (M−H$^+$), 360, 358.

EXAMPLE 2.08

3-Bromo-5-Fluoro-N-(3-trifluoromethyphenylsulphonyl)indole-2-carboxylic acid in 69% yield NMR δ (CD$_3$SOCD$_3$) 7.32–7.46 (m, 2H), 7.88 (t, 1H), 8.08–8.16 (m, 2H), 8.31–8.37 (m, 2H); M/z(−) 466 (M−H$^+$), 404, 422, 420.

EXAMPLE 3

Methyl N-(3,4-dichlorophenylsulphonyl)4-hydroxyindole-2-carboxylate

Aqueous sodium hydrogencarbonate solution (16 ml, 50%) was added to methyl 4-acetoxy-N-(3,4-dichlorophenylsulphonyl)indole-2-carboxylate (0.63 g) in methanol (15 ml) and the reaction stirred for 48 hours at room temperature. The solution was then poured into 2M HCl and extracted with ethyl acetate. Combined organic extracts were dried (MgSO$_4$) and concentrated in vacuo to give the desired product as a gum (0.5 g, 87%); NMR δ (CD$_3$SOCD$_3$) 3.83 (s, 3H), 6.71 (d, 1H), 7.31 (t, 1H), 7.42–7.5 (m, 2H), 7.92 (s, 1H), 10.31 (s, 1H); M/z (+) 402 (MH$^+$), 400.

Preparation of Starting Materials

Starting materials for the Examples above are either commercially available or are readily prepared by standard methods from known materials, for example the following reactions (Methods A to F) are illustrations but not limitations of the preparation of some of the starting materials used in the above reactions.

Method A

6-Bromo-2-naphthylsulphonyl chloride

A solution of sodium nitrite (2.7 g) in water (5 ml) was added during 2 hours to a stirred mixture of 6-amino-2-naphthalene-sulphonic acid (8.8 g), dilute aqueous hydrochloric acid (2.8% weight/volume, 20 ml) and water (15 ml) which had been cooled to 0° C. The mixture was stirred at 0° C. for 30 minutes and poured onto a stirred suspension of cuprous bromide (5.34 g) in dilute aqueous hydrobromic acid (2.8%, 20 ml). The mixture was stored at ambient temperature for 18 hours. The mixture was evaporated to give 6-bromo-2-naphthalenesulphonic acid which was used without further purification.

The material was suspended in DMF (40 ml) and cooled to 5° C. Thionyl chloride (8.6 ml) was added dropwise and the mixture was stirred at 5° C. for 3 hours. The mixture was poured onto ice and extracted with methylene chloride. The organic solution was dried (MgSO$_4$) and evaporated. The residue was purified by column chromatography using a 20:1 mixture of hexane and ethyl acetate as eluent to give the desired starting material in 22% yield. NMR δ (CD$_3$SOCD$_3$) 7.65 (m, 1H), 7.75–8.0 (m, 3H), 8.15–8.2 (m, 2H).

Method B

Ethyl 3-bromoindole-2-carboxylate

A solution of bromine (2.72 ml) in DMF was added dropwise over 10 mins to a solution of ethyl indole-2-carboxylate in DMF. The reaction was stirred for 30 mins, then poured into water to precipitate a pale yellow solid which was filtered off and recrystallized from ethyl acetate to give the desired starting material as white needles (10.2 g, 72%), mp 150–151°; NMR δ (CDCl$_3$) 1.44 (t, 3H), 4.45 (q, 2H), 7.22 (m, 1 H), 7.38 (m, 2H), 7.66 (d, 1H), 9.27 (bs, 1H); M/z(−) 268 (M$^+$), 266, 196, 194.

The procedure described above was repeated using the appropriate indole. Thus was obtained the compound described below.

Methyl 3-bromo-5-fluoroindole-2-carboxylate in 83% yield

NMR δ (CD$_3$SOCD$_3$) 3.9 (s, 3H), 7.08–7.28 (m, 2H), 7.49 (dd, 1H), 12.38 (bs, 1H); M/z (+) 274 (MH$^+$), 272.

Method C

Ethyl 3-chloroindole-2-carboxylate

Ethyl 3-chloroindole-2-carboxylate (3 g) and phosphorous pentachloride (9 g) were heated at 90° C. for 1 hour. The mixture was then cooled to room temperature, poured into water and the resulting solid filtered purified by column chromatography using isohexane-20% ethyl acetate as eluent to give the desired end product as a white solid (1.25 g, 35%); NMR δ (CD$_3$SOCD$_3$) 1.3 (t, 3H), 4.4 (q, 2H), 7.2 (t, 1H), 7.35 (t, 1H), 7.45 (d, 1H), 7.6 (d, 1H), 12.5 (1H, bs); M/z (−) 222 (M−H$^+$).

Method D

Methyl-5-chloroindole-2-carboxylate

Sodium (10.3 g, 447 mmol) was dissolved in methanol (HPLC grade, anhydrous, 150 ml) with continual stirring under an atmosphere of argon. Upon complete dissolution of the sodium ethyl-5-chloroindole-2-carboxylate (10.08 g, 44.7 mmol) was added as a single portion and the reaction mixture was stirred at room temperature for 2 hours. The reaction mixture was acidified with the addition of aqueous hydrochloric acid (excess) causing the precipitation of a white solid. The solid was filtered and washed with aqueous hydrochloric acid (100 ml) and water (100 mls) then dried overnight in at 55° to yield the product as a white solid (8.97 g, 95%). NMR δ (CD$_3$SOCD$_3$) 3.86 (s, 3H), 7.12 (dd, 1H), 7.24 (dd, 1H), 7.43 (d, 1H), 7.72 (s, 1H), 12.10 (brs, 1H).

The procedure described above was repeated using the appropriate indole. Thus was obtained the compound described below.

Methyl 3-bromoindole-2-carboxylate in 79% yield

NMR δ (CD$_3$SOCD$_3$) 3.90 (s, 3H), 7.18 (t, 1H), 7.35 (t, 1H), 7.47 (d, 1H), 7.53 (d, 1H), 12.24 (brs, 1H).

Methyl 3-chloroindole-2-carboxylate in 64% yield

NMR δ (CD$_3$SOCD$_3$) 3.90 (s, 3H), 7.18 (t, 1H), 7.35 (t, 1H), 7.45 (d, 1H), 7.59 (d, 1H); M/z (+) 212 (MH$^+$), 210.

Method E

Methyl 4-hydroxyindole-2-carboxylate

Boron tribromide (73.1 ml, 1.0 M solution in DCM) was added dropwise to a solution of methyl 4-methoxyindole-2-carboxylate (5 g) in DCM (200 ml) cooled to −78° C. under argon. The reaction was allowed to warm to room temperature then partitioned between dichloromethane and saturated aqueous sodium hydrogen carbonate solution. Combined organic extracts were dried (MgSO$_4$) and concentrated in vacuo and the residue purified by column chromatography using isohexane-50% ethyl acetate as eluent to give the end product as a yellow solid (2.98 g, 64%); NMR δ (CD$_3$SOCD$_3$) 3.82 (s, 3H), 6.36 (d, 1H), 6.85 (d, 1H), 7.02 (t, 1H), 7.17 (d, 1H), 9.66 (s, 1H), 11.72 (bs, 1H); M/z (+) 192 (MH$^+$).

Method F

Methyl 4-acetoxyindole-2-carboxylate

Methyl 4-hydroxyindole-2-carboxylate (0.5 g) and 4-dimethylarninopyridine (50 mg) were dissolved in acetic anhydride (5 ml) and heated at 80° C. for 3 hours. The reaction was allowed to cool overnight to precipitate white crystals, which were filtered and dried in vacuo (0.44 g, 72%); NMR δ (CD$_3$SOCD$_3$) 2.34 (s, 3H), 3.85 (s, 3H), 6.80 (d, 1H), 7.06 (s, 1H), 7.23 (t, 1H), 7.29–7.35 (m, 1H), 12.1 (bs, 1H); M/z (−) 232 (M−H$^+$).

What we claim is:

1. A compound of the formula (I):

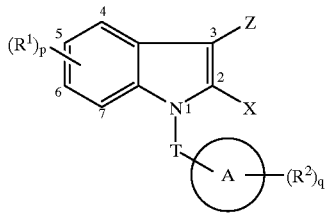

wherein

R$^1$ is independently selected from trifluoromethyl, C$_{1-4}$alkyl, halo, hydroxy, C$_{1-4}$alkoxy, C$_{1-4}$alkanoyl, C$_{1-4}$alkanoyloxy, amino, cyano, C$_{1-4}$alkylamino, di(C$_{1-4}$ alkyl)amino, C$_{1-4}$alkanoylamino, nitro, carbamoyl, C$_{1-4}$alkoxycarbonyl, thiol, C$_{1-4}$alkylsulphanyl, C$_{1-4}$alkylsulphinyl, C$_{1-4}$alkylsulphonyl, sulphonamido, carbamoylC$_{1-4}$ alkyl, N—(C$_{1-4}$alkyl)carbamoylC$_{1-4}$ alkyl, N—(C$_{1-4}$alkyl)$_2$carbarnoyl-C$_{1-4}$alkyl, hydroxyC$_{1-4}$alkyl, C$_{1-4}$alkoxyC$_{1-4}$alkyl, morpholino, pyrrolidinyl, carboxyC$_{1-4}$alkylamino, R$^3$ and —OR$^3$ (where R$^3$ is optionally substituted aryl or an optionally substituted 5- or 6-membered heteroaryl ring);

p is 1–4 and R$^1$ may have the same or different values when p is 2–4;

T is of the formula

(where R$^4$ is independently selected from hydrogen or C$_{1-4}$alkyl, m=0–2, s=0–2, m+s=0–2, and R$^4$ may take different values when m+s=2;

X is carboxyl, tetrazol-5-yl, cyano, SO$_3$H, —SO$_2$NHR$^4$ (where R$^4$ is as defined above), —SO$_2$NHAr (where Ar is an optionally substituted phenyl or optionally substituted 5 or 6 membered heteroaryl ring), —CONHR$^5$ (where R$^5$ is H, cyano, OH, —SO$_2$—C$_{1-4}$alkyl, —SO$_2$CF$_3$, —SO$_2$-phenyl, —(CHR$^4$)$_r$—COOH, (where r is 1–3 and R$^4$ (as defined above) may take different values when r is 2–3)), or X is a group of formula (II)

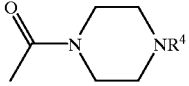

or X represents a group of formula (III)

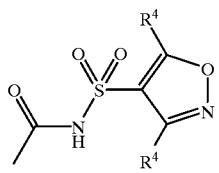

where the groups defined as R$^4$ may have different values within the definition of R$^4$ above;

A is selected from phenyl, naphthyl, furyl, pyridyl and thienyl;

R$^2$ is independently selected from trifluoromethyl, propyl, isopropyl, t-butyl, cyclopropyl, halo, hydroxy, trifluoromethoxy, cyano, C$_{1-4}$alkoxy, C$_{1-4}$alkanoyl, C$_{1-4}$alkanoyloxy, amino, C$_{1-4}$alkylamino, di(C$_{1-4}$alkyl) amino, C$_{1-4}$alkanoylamino, nitro, carboxy, carbamoyl, C$_{1-4}$alkoxycarbonyl, thiol, C$_{1-4}$alkylsulphanyl, C$_{1-4}$alkylsulphinyl, C$_{1-4}$alkylsulphonyl, sulphonamido, carbamoylC$_{1-4}$alkyl, N—(C$_{1-4}$alkyl)carbamoylC$_{1-4}$ alkyl, N—(C$_{1-4}$alkyl)$_2$carbamoyl-C$_{1-4}$alkyl, hydroxyC$_{1-4}$alkyl, C$_{1-4}$alkoxyC$_{1-4}$alkyl or two R$^2$ values together may form a divalent radical of the formula —O(CH$_2$)$_{1-4}$O— attached to adjacent carbon atoms on ring A;

q is 1–4 and R$^2$ may have the same or different values when q is 2–4;

Z is hydrogen, fluoro, chloro, bromo, iodo, methyl, trifluoromethyl, hydroxymethyl, methoxy, methylsulphanyl, methylsulphinyl, methylsulphonyl or carboxyC$_{3-6}$cycloalkyl, —(CHR$^4$)r-NR$^6$R$^7$ (where r is 0–2, R$^6$ and R$^7$ are independently selected from H and C$_{1-4}$alkyl or R$^6$ and R$^7$ together with the nitrogen to which they are attached form a 5 or 6 membered non-aromatic ring optionally containing one further heteroatom selected from O, N or S);

or a pharmaceutically acceptable salt or an *in vivo* hydrolysable ester thereof.

2. A compound of formula (I'):

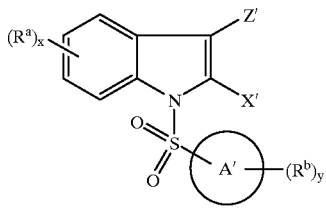

(I')

wherein $R^a$ is methoxy, fluoro, chloro, bromo, nitro, amino, phenoxy, trifluoromethyl, or carboxymethylamino;

x is 1 or 2 with the proviso that there is at most one methoxy group;

X' is carboxy, —CONHSO$_2$CF$_3$ or tetrazol-5-yl:

A' is phenyl or thienyl;

$R^b$ is chloro, bromo, methoxy, nitro, trifluoromethyl or trifluoromethoxy;

y is 1 or 2;

Z' is hydrogen or bromo;

or a pharmaceutically acceptable salt or in vivo hydrolysable ester thereof.

3. A compound as claimed in claim 1 or 2 wherein $A(R^2)_q$ or $A'(R^b)_y$ is 3-chlorophenyl, 4-chlorophenyl, 3-fluorophenyl, 4-fluorophenyl, 3-trifluoromethylphenyl, 3,4-dichlorophenyl or 3,4-difluorophenyl.

4. A compound as claimed in claim 1 or 2 wherein X or X' is carboxy.

5. A compound as claimed in claim 1 which is selected from

N-(3,4-dichlorophenylsulphonyl)-5-chloroindole-2-carboxylic acid;

N-(6-bromonaphthalene-2-ylsulphonyl)-5-chloroindole-2-carboxylic acid;

N-(3-chlorophenylsulphonyl)-5-chloroindole-2-carboxylic acid; and 3-bromo-5-fluoro-N-(3-trifluoromethylphenylsulphonyl)indole-2-carboxylic acid;

or an in vivo hydrolysable ester or a pharmaceutically acceptable salt thereof.

6. A pharmaceutical composition which comprises a compound of the formula (I), or a pharmaceutically acceptable salt or in vivo hydrolysable ester thereof, together with a pharmaceutically acceptable diluent or carrier.

7. A compound of the formula (IA)

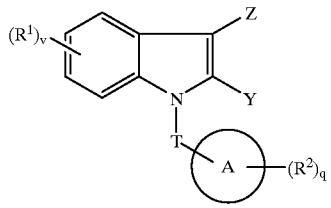

(IA)

wherein $R^1$ is attached at the 4 and/or 5 position of the indol ring, and is independently selected from trifluoromethyl, C$_{1-4}$alkyl, halo, hydroxy, C$_{1-4}$alkoxy, C$_{1-4}$alkanoyl, C$_{1-4}$alkanoyloxy, amino, cyano, C$_{1-4}$alkylamino, di(C$_{1-4}$ alkyl)amino, C$_{1-4}$alkanoylamino, nitro, carbamoyl, C$_{1-4}$alkoxycarbonyl, thiol, C$_{1-4}$alkylsulphanyl, C$_{1-4}$alkylsulphinyl, C$_{1-4}$alkylsulphonyl, sulphonamido, carbamoylC$_{1-4}$alkyl, N—(C$_{1-4}$alkyl$_2$carbamoyl-C$_{1-4}$ alkyl, hydroxyC$_{1-4}$alkyl, C$_{1-4}$alkoxyC$_{1-4}$alkyl, morpholino, pyrrolidinyl, carboxyC$_{1-4}$alkylamino, R$^3$ and —OR$^3$ (where R$^3$ is optionally substituted phenyl or an optionally substituted 5- or 6-membered heteroaryl ring);

v is 1 or 2;

Z is hydrogen, fluoro, chloro, bromo, iodo, methyl, trifluoromethyl, hydroxymethyl, methoxy, methylsulphanyl, methylsulphinyl, methylsulphonyl or carboxyC$_{3-6}$cycloalkyl, —(CHR$^4$)$_r$—NR$^6$R$^7$ (where r is 0–2, R$^6$ and R$^7$ are independently selected from H and C$_{1-4}$alkyl or R$^6$ and R$^7$ together with the nitrogen to which they are attached form a 5 or 6 membered non-aromatic ring optionally containing one further heteroatom selected from O, N or S);

Y is carboxy;

T is —SO$_2$—; and $A(R^2)_q$ is phenyl independently substituted at the 3 and 4 positions by halogeno;

or a pharmaceutically acceptable salt or an in vivo hydrolysable ester thereof.

8. A compound of the formula (IA) as defined in claim 7 which is selected from

N-(3-chlorophenylsulphonyl)indole-2-carboxylic acid;

N-(3,4dichlorophenylsulphonyl)indole-2-carboxylic acid;

N-(4,5-dichlorothien-2-ylsulphonyl)indole-2-carboxylic acid;

3-bromo-N-(3-trifluoromethylphenylsulphonyl)indole-2-carboxylic acid; and 3-chloro-N-(3-trifluoromethylphenylsulphonyl)indole-2-carboxylic acid; or a pharmaceutically acceptable salt thereof or an in vivo hydrolysable ester thereof.

9. A pharmaceutical composition which comprises a compound as claimed in claim 7 or 8, or a pharmaceutically acceptable salt thereof or in vivo hydrolysable ester thereof, together with a pharmaceutically acceptable diluent or carrier.

10. A method for antagonising an MCP-1 mediated effect in a warm blooded animal in need thereof, comprising administering to said animal an effective amount of a compound of the formula (IA)

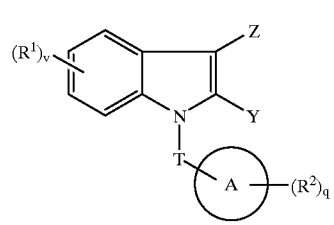

(IA)

wherein $R^1$ is independently selected from trifluoromethyl, C$_{1-4}$alkyl, halo, hydroxy, C$_{1-4}$alkoxy, C$_{1-4}$alkanoyl, C$_{1-4}$alkanoyloxy, anino, cyano, C$_{1-4}$alkylamino, di(C$_{1-4}$ alkyl)amino, C$_{1-4}$alkanoylamino, nitro, carbamoyl, C$_{1-4}$alkoxycarbonyl, thiol, C$_{1-4}$alkylsulphanyl, C$_{1-4}$alkylsulphinyl, C$_{1-4}$alkylsulphonyl, sulphonamido, carbamoylC$_{1-4}$ alkyl, N—($C_{1-4}$alkyl)$_2$carbamoyl-$C_{1-4}$ alkyl, hydroxy$C_{1-4}$alkyl, $C_{1-4}$alkoxy$C_{1-4}$alkyl, morpholino, pyrrolidinyl, carboxy$C_{1-4}$alkylamino, $R^3$ and —$OR^3$ (where $R^3$ is optionally substituted phenyl or an optionally substituted 5- or 6- membered heteroaryl ring);

v is 0–4;

$R^2$ is independently selected from trifluoromethyl, $C_{1-4}$alkyl, halo, hydroxy, trifluoromethoxy, cyano, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, carboxy, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl$C_{1-4}$alkyl, N—($C_{1-4}$alkyl)carbamoyl$C_{1-4}$alkyl, N—($C_{1-4}$alkyl)$_2$carbamoyl-$C_{1-4}$alkyl, hydroxy$C_{1-4}$alkyl, $C_{1-4}$alkoxy$C_{1-4}$alkyl or two $R^2$ values together may form a divalent radical of the formula —$O(CH_2)_{1-4}O$— attached to adjacent carbon atoms on ring A;

q is 0–4 and each $R^2$ can have the same or different value when q is 2–4;

Z is hydrogen, fluoro, chloro, bromo, iodo, methyl, trifluoromethyl, hydroxymethyl, methoxy, methylsulphanyl, methylsulphinyl, methylsulphonyl or carboxy$C_{3-6}$cycloalkyl, —$(CHR^4)_r$—$NR^6R^7$ (where r is 0–2, $R^6$ and $R^7$ are independently selected from H and $C_{1-4}$alkyl or $R^6$ and $R^7$ together with the nitrogen to which they are attached form a 5 or 6 membered non-aromatic ring optionally containing one further heteroatom selected from O, N or S);

Y is carboxyl, tetrazol-5-yl, cyano, $SO_3H$, —$SO_2NHR^4$ (where $R^4$ is as defined above), —$SO_2NHAr$ (where Ar is an optionally substituted phenyl or optionally substituted 5 or 6 membered heteroaryl ring), —$CONHR^5$ (where $R^5$ is cyano, OH, —$SO_2$—$C_{1-4}$alkyl, —$SO_2CF_3$, —$SO_2$-phenyl, —$(CHR^4)_r$—COOH, (where r is 1–3 and $R^4$ (as defined above) can take different values when r is 2–3)), or X represents a group of the formula (II)

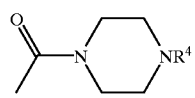

(II)

or X represents a group of formula (III)

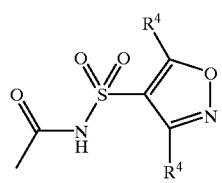

(III)

where the groups defined as $R^4$ here may have different values within the definition of $R^4$ above; or Y is —$CONHR^{10}$ where $R^{10}$ is H or $C_{1-4}$alkyl;

T is of the formula

—$(CHR^4)_m$—$(SO_2)$—$(CHR^4)_s$—

(where $R^4$ is hydrogen or $C_{1-4}$alkyl, m=0–2, s=0–2, m+s= 0–2, and $R^4$ can take different values when m+s=2);

A is selected from phenyl, naphthyl, furyl, pyridyl and thienyl;

or a pharmaceutically acceptable salt or an in vivo hydrolysable ester thereof.

11. A compound of the formula (I):

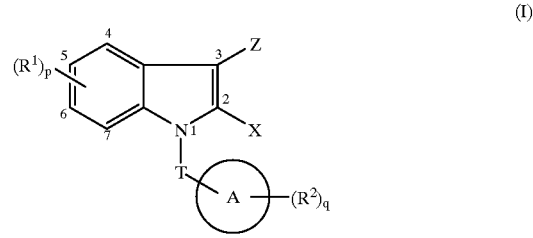

(I)

wherein $R^1$ is independently selected from trifluoromethyl, $C_{1-4}$alkyl, halo, hydroxy, $C_{1-4}$alkoxy, $C_{1-4}$alkanoyl, $C_{1-4}$alkanoyloxy, amino, cyano, $C_{1-4}$alkylamino, di($C_{1-4}$ alkyl)amino, $C_{1-4}$alkanoylamino, nitro, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl$C_{1-4}$alkyl, N—($C_{1-4}$alkyl)carbamoyl$C_{1-4}$alkyl, N—($C_{1-4}$alkyl)$_2$carbarnoyl-$C_{1-4}$alkyl, hydroxy$C_{1-4}$alkyl, $C_{1-4}$alkoxy$C_{1-4}$alkyl, morpholino, pyrrolidinyl, carboxy$C_{1-4}$alkylamino, $R^3$ and —$OR^3$ (where $R^3$ is optionally substituted aryl or an optionally substituted 5- or 6-membered heteroaryl ring);

p is 1–4 and $R^1$ may have the same or different values when p is 2–4;

T is of the formula $(CHR^4)_m$—$(SO_2)$—$(CHR^4)_s$—

(where $R^4$ is independently selected from hydrogen or $C_{1-4}$alkyl, m=0–2, s=0–2, m+s=0–2, and $R^4$ may take different values when m+s=2;

X is carboxyl, tetrazol-5-yl, cyano, $SO_3H$, —$SO_2NHR^4$ (where $R^4$ is as defined above), —$SO_2NHAr$ (where Ar is an optionally substituted phenyl or optionally substituted 5 or 6 membered heteroaryl ring), —$CONHR^5$ (where $R^5$ is H, cyano, OH, —$SO_2$—$C_{1-4}$alkyl, —$SO_2CF_3$, —$SO_2$-phenyl, —$(CHR^4)_r$—COOH, (where r is 1–3 and $R^4$ (as defined above) may take different values when r is 2–3)), or X is a group of formula (II)

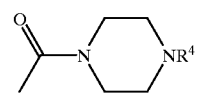

(II)

or X represents a group of formula (III)

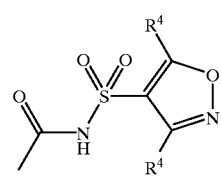

(III)

where the groups defined as $R^4$ may have different values within the definition of $R^4$ above;

A is selected from naphthyl, furyl, pyridyl and thienyl;

$R^2$ is independently selected from trifluoromethyl, $C_{1-4}$alkyl, halo, hydroxy, trifluoromethoxy, cyano, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, carboxy, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl$C_{1-4}$alkyl, N—($C_{1-4}$alkyl)carbamoyl$C_{1-4}$alkyl, N—($C_{1-4}$alkyl)$_2$carbamoyl-$C_{1-4}$alkyl, hydroxy$C_{1-4}$alkyl, $C_{1-4}$alkoxy$C_{1-4}$alkyl or two $R^2$ values together may form a divalent radical of the formula —O(CH$_2$)$_{1-4}$O— attached to adjacent carbon atoms on ring A;

q is 0–4 and $R^2$ may have the same or different values when q is 2–4;

Z is hydrogen, fluoro, chloro, bromo, iodo, methyl, trifluoromethyl, hydroxymethyl, methoxy, methylsulphanyl, methylsulphinyl, methylsulphonyl or carboxy$C_{3-6}$cycloalkyl, —(CHR$^4$)r-NR$^6$R$^7$ (where r is 0–2, R$^6$ and R$^7$ are independently selected from H and $C_{1-4}$alkyl or R$^6$ and R$^7$ together with the nitrogen to which they are attached form a 5 or 6 membered non-aromatic ring optionally containing one further heteroatom selected from O, N or S);

or a pharmaceutically acceptable salt or an in vivo hydrolysable ester thereof.

12. A compound of the formula (I):

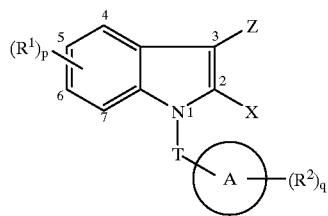

(I)

wherein $R^1$ is independently selected from trifluoromethyl, $C_{1-4}$alkyl, halo, hydroxy, $C_{1-4}$alkoxy, $C_{1-4}$alkanoyl, $C_{1-4}$alkanoyloxy, amino, cyano, $C_{1-4}$alkylamino, di($C_{1-4}$ alkyl)amino, $C_{1-4}$alkanoylamino, nitro, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl$C_{1-4}$alkyl, N—($C_{1-4}$alkyl)carbamoyl$C_{1-4}$ alkyl, N—($C_{1-4}$alkyl)$_2$carbarnoyl-$C_{1-4}$alkyl, hydroxy$C_{1-4}$alkyl, $C_{1-4}$alkoxy$C_{1-4}$alkyl, morpholino, pyrrolidinyl, carboxy$C_{1-4}$alkylamino, $R^3$ and —OR$^3$ (where $R^3$ is optionally substituted aryl or an optionally substituted 5- or 6-membered heteroaryl ring);

p is 1–4 and $R^1$ may have the same or different values when p is 2–4;

T is of the formula

(where $R^4$ is independently selected from hydrogen or $C_{1-4}$alkyl, m=0–2, s=0–2, m+s=0–2, and $R^4$ may take different values when m+s=2;

X is carboxyl, tetrazol-5-yl, cyano, SO$_3$H, —SO$_2$NHR$^4$ (where R$^4$ is as defined above), —SO$_2$NHAr (where Ar is an optionally substituted phenyl or optionally substituted 5 or 6 membered heteroaryl ring), —CONHR$^5$ (where R$^5$ is H, cyano, OH, —SO$_2$—$C_{1-4}$alkyl, —SO$_2$CF$_3$, —SO$_2$-phenyl, —(CHR$^4$)$_r$—COOH, (where r is 1–3 and R$^4$ (as defined above) may take different values when r is 2–3)), or X is a group of formula (II)

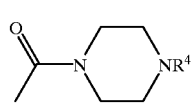

(II)

or X represents a group of formula (III)

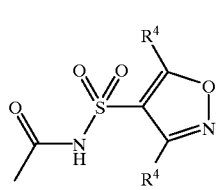

(III)

where the groups defined as $R^4$ may have different values within the definition of $R^4$ above;

A is selected from phenyl, naphthyl, furyl, pyridyl and thienyl;

$R^2$ is independently selected from trifluoromethyl, $C_{1-4}$alkyl, halo, hydroxy, trifluoromethoxy, cyano, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, carboxy, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl$C_{1-4}$alkyl, N—($C_{1-4}$alkyl)carbamoyl$C_{1-4}$ alkyl, N—($C_{1-4}$alkyl)$_2$carbamoyl-$C_{1-4}$alkyl, hydroxy$C_{1-4}$alkyl, $C_{1-4}$alkoxy$C_{1-4}$alkyl or two $R^2$ values together may form a divalent radical of the formula —O(CH$_2$)$_{1-4}$O— attached to adjacent carbon atoms on ring A;

q is 2–4 and $R^2$ may have the same or different values;

Z is hydrogen, fluoro, chloro, bromo, iodo, methyl, trifluoromethyl, hydroxymethyl, methoxy, methylsulphanyl, methylsulphinyl, methylsulphonyl or carboxy$C_{3-6}$cycloalkyl, —(CHR$^4$)r-NR$^6$R$^7$ (where r is 0–2, R$^6$ and R$^7$ are independently selected from H and $C_{1-4}$alkyl or R$^6$ and R$^7$ together with the nitrogen to which they are attached form a 5 or 6 membered non-aromatic ring optionally containing one further heteroatom selected from O, N or S);

or a pharmaceutically acceptable salt or an *in vivo* hydrolysable ester thereof.

13. A compound of formula (I'):

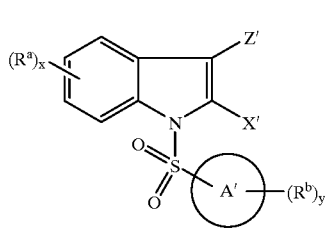

(I')

wherein $R^a$ is methoxy, bromo, nitro, amino, phenoxy, trifluoromethyl, or carboxymethylamino;

x is 1 or 2 with the proviso that there is at most one methoxy group;

X' is carboxy, —CONHSO$_2$CF$_3$ or tetrazol-5-yl:

A' is phenyl or thienyl;

R$^b$ is chloro, bromo, methyl, methoxy, nitro, trifluoromethyl or trifluoromethoxy;

y is 1 or 2;

Z' is hydrogen or bromo;

or a pharmaceutically acceptable salt or in vivo hydrolysable ester thereof.

14. A compound of formula (I'):

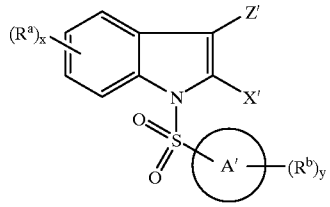

(I')

wherein

R$^a$ is methoxy, fluoro, chloro, bromo, nitro, amino, phenoxy, trifluoromethyl, or carboxymethylamino;

x is 1 or 2 with the proviso that there is at most one methoxy group;

X' is carboxy, —CONHSO$_2$CF$_3$ or tetrazol-5-yl:

A' is thienyl;

R$^b$ is chloro, bromo, methyl, methoxy, nitro, trifluoromethyl or trifluoromethoxy;

y is 1 or2;

Z' is hydrogen or bromo;

or a pharmaceutically acceptable salt or in vivo hydrolysable ester thereof.

15. A compound is claimed in claim 12 wherein A(R$^2$)$_q$ is 3,4-dichlorophenyl or 3,4-difluorophenyl.

16. A compound is claimed in claim 13 wherein A'(R$^b$)$_y$ is 3-chlorophenyl, 4-chlorophenyl, 3-fluorophenyl, 4-fluorophenyl, 3-trifluoromethylphenyl, 3,4-dichlorophenyl or 3,4-difluorophenyl.

17. A compound as claimed in any one of claims 11, 12, 13 or 14 wherein X or X' is carboxy.

* * * * *